US008744565B2

(12) United States Patent
Zielinski et al.

(10) Patent No.: US 8,744,565 B2
(45) Date of Patent: Jun. 3, 2014

(54) MULTI-FREQUENCY IMPEDANCE MONITORING SYSTEM

(75) Inventors: Todd M. Zielinski, Ham Lake, MN (US); Douglas A. Hettrick, Andover, MN (US); Shantanu Sarkar, Roseville, MN (US)

(73) Assignee: Medtronic, Inc., Minneapolis, MN (US)

( * ) Notice: Subject to any disclaimer, the term of this patent is extended or adjusted under 35 U.S.C. 154(b) by 1514 days.

(21) Appl. No.: 12/112,765

(22) Filed: Apr. 30, 2008

(65) Prior Publication Data

US 2009/0275855 A1 Nov. 5, 2009

(51) Int. Cl.
*A61B 5/00* (2006.01)

(52) U.S. Cl.
USPC .......................................... 600/547

(58) Field of Classification Search
USPC .......... 600/300, 544–548, 554, 587; 607/1–3, 607/39–76
See application file for complete search history.

(56) References Cited

U.S. PATENT DOCUMENTS

| 3,593,718 | A | 7/1971 | Krasner et al. |
| 4,223,678 | A | 9/1980 | Langer et al. |
| 4,596,351 | A | 6/1986 | Fedotov et al. |
| 4,702,253 | A | 10/1987 | Nappholz et al. |
| 4,757,815 | A | 7/1988 | Strandberg et al. |
| 4,793,362 | A | 12/1988 | Tedner |
| 4,805,621 | A | 2/1989 | Heinze et al. |
| 4,840,182 | A | 6/1989 | Carlson |
| 4,919,136 | A | 4/1990 | Alt |
| 5,027,813 | A | 7/1991 | Pederson et al. |
| 5,080,586 | A | 1/1992 | Kawai |
| 5,282,840 | A | 2/1994 | Hudrlik |
| 7,186,220 | B2 | 3/2007 | Stahmann et al. |
| 2006/0041280 | A1 | 2/2006 | Stahmann et al. |
| 2006/0184060 | A1 | 8/2006 | Belalcazar et al. |

FOREIGN PATENT DOCUMENTS

| EP | 1582233 | 10/2005 |
| WO | 0119426 | 3/2001 |

OTHER PUBLICATIONS

International Search Report, PCT/US2009/039314, 4 pages.

*Primary Examiner* — Max Hindenburg
(74) *Attorney, Agent, or Firm* — Reed A. Duthler

(57) ABSTRACT

A system and method is provided to measure intrathoracic complex impedance and to identify and indicate disease conditions based on the impedance measurements. Multiple impedance vectors may be taken into account, and an optimal vector may be selected to provide the most useful impedance measurement for the identification and indication of disease conditions.

2 Claims, 22 Drawing Sheets

MULTI-FREQUENCY IMPEDANCE MONITORING SYSTEM

CROSS-REFERENCE TO RELATED APPLICATION(S)

Reference is hereby made to the U.S. application Ser. No. 12/112,655 filed on even date herewith, for "System And Method Of Detecting Physiologic Parameters Based On Complex Impedance Waveform Morphology" by T. Zielinski, D. Hettrick and E. Warman, which is hereby incorporated by reference in its entirety.

BACKGROUND

The present invention relates to systems and methods for measuring intrathoracic impedance (intracardiac, intravascular, subcutaneous, etc.) in an implantable medical device (IMD) system.

In systems employing IMDs such as pacemakers, defibrillators, and others, it has proven beneficial to provide the ability to measure intrathoracic impedance. Intrathoracic impedance measuring is performed by monitoring the voltage differential between pairs of spaced electrodes as current pulses are injected into those same leads or into other electrodes. Changes in the measured intrathoracic impedance may indicate certain disease conditions that can be addressed by delivery of therapy or alarm notification, for example. The efficacy of impedance monitoring to evaluate and monitor pulmonary edema and worsening congestive heart failure has been demonstrated in the OptiVol® Fluid Status Monitoring system provided by Medtronic, Inc. of Minneapolis, Minn.

Further improvements in the ability of an intrathoracic impedance measuring system to identify and monitor disease conditions would be useful.

SUMMARY

A system and method is provided to measure intrathoracic impedance and to identify and monitor disease conditions based on the impedance measurements. Multiple electrode combinations may be taken into account, and an optimal combination of electrodes may be selected to provide the most useful (e.g., sensitive and specific) impedance measurement for the identification and monitoring of disease conditions.

DETAILED DESCRIPTION

Figure 1:
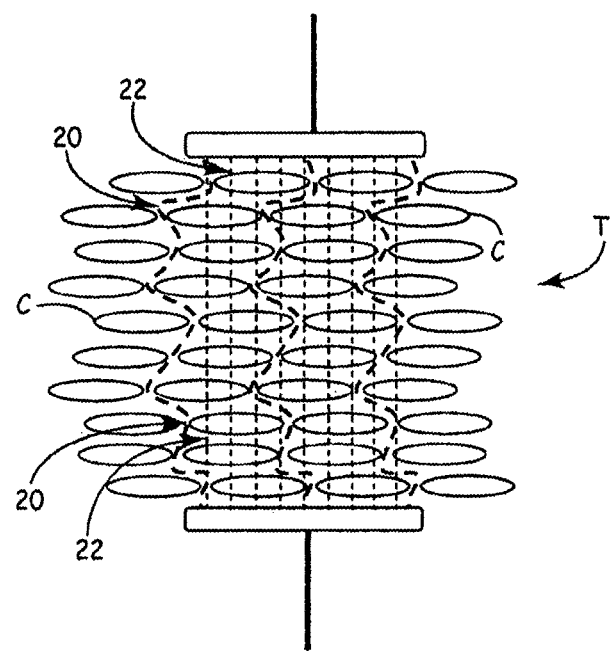
FIG. 1 is a diagram depicting the paths taken by low frequency current and high frequency current injected through a homogenous tissue segment.

FIG. 1 is a diagram depicting path 20 taken by low frequency current injected through a selected tissue segment T, and path 22 taken by high frequency current injected through tissue segment T. Low frequency current flows primarily in path 20 through extracellular spaces in tissue segment T, due to the frequency dependent resistance provided by the cellular membrane of cells C. By contrast, high frequency current reduces the capacitive reactance component of the cellular membrane of cells C, allowing current to flow more uniformly through tissue segment T. This difference in the response of tissue segment T to currents of different frequencies can be utilized to identify and predict disease conditions, examples of which are discussed in detail below.

Figure 2:
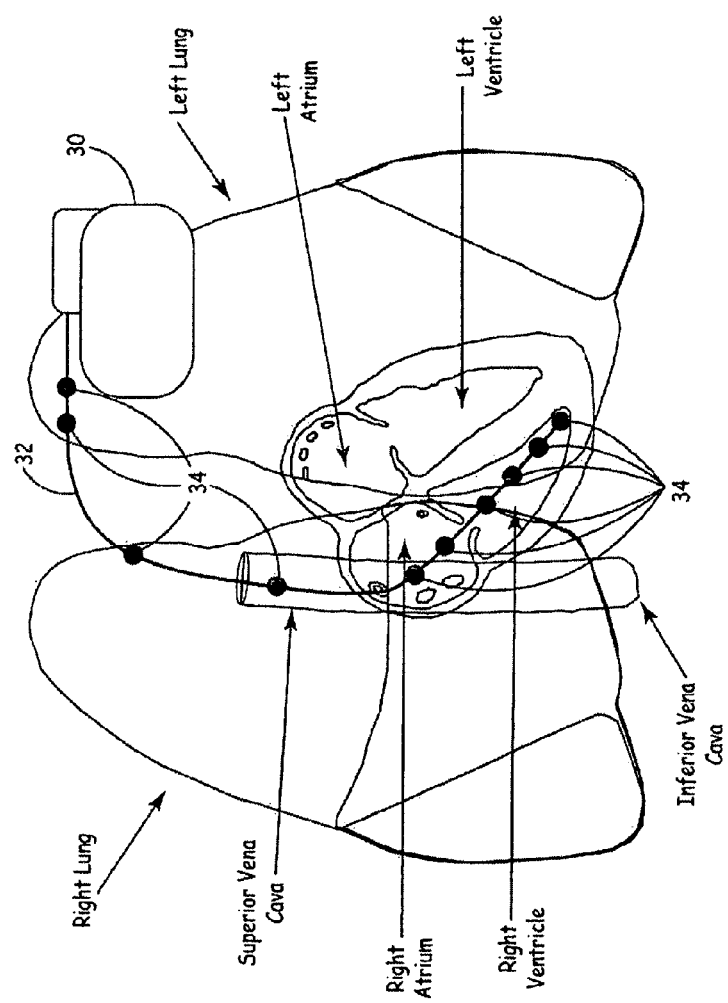
FIG. 2 is a diagram illustrating an example of the relative placement of an IMD and a lead carrying electrodes for performing an intrathoracic impedance measurement.

FIG. 2 is a diagram illustrating an example of the relative placement of IMD 30 and lead 32 carrying electrodes 34 for performing an intrathoracic impedance measurement IMD 30 is implantable under the skin of a patient in the chest area, and includes impedance measurement circuitry and processing circuitry, as well as various leads for sensing and therapy delivery functions. In FIG. 2, for example, lead 32 is shown extending into the right ventricle (RV), with electrodes 34 positioned in the RV, the right atrium, the superior vena cava and the subclavian vein. By injecting a current between selected electrodes 34, a voltage differential between those electrodes can be created that allows the impedance of the tissue between the electrodes to be measured. Many other configurations and arrangements of electrodes 34, leads 32, and IMD 30 are possible, and other examples are discussed in a later section below.

Measurement of Impedance Magnitude Differences at Low and High Frequencies

Figure 3:
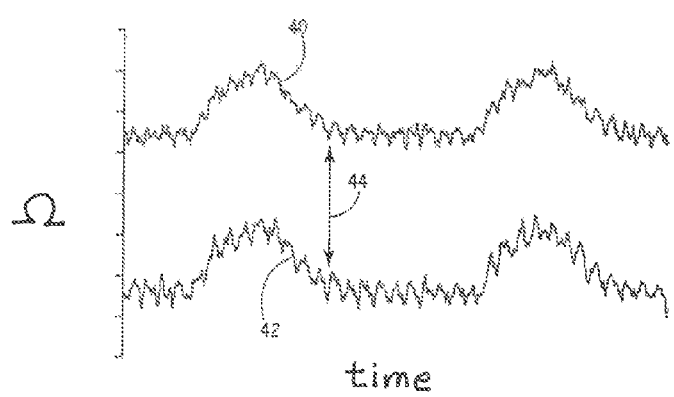
FIG. 3 is a graph illustrating the magnitude of the impedance measured between electrodes in a homogenous tissue segment for a low frequency injection current and a high frequency injection current.

FIG. 3 is a graph illustrating the magnitude of the impedance measured between electrodes in a tissue segment (such as between selected electrodes 34 shown in FIG. 2) for a low frequency injection current (curve 40) and a high frequency injection current (curve 42). As discussed above with respect to FIG. 1, low frequency current flows primarily through extracellular spaces in tissue, while high frequency current reduces the capacitive reactance component of the cellular membranes, allowing current to flow more uniformly through the tissue. Thus, the impedance measured in response to the low frequency injection current is larger than the impedance measured in response to the high frequency injection current. Moreover, the difference 44 between the low frequency impedance and the high frequency impedance of the tissue is indicative of the state of the tissue. Specifically, the progression of pulmonary edema causes the difference between the low frequency impedance magnitude and the high frequency impedance magnitude to decrease, due to the accumulation of fluid in the extracellular spaces. Thus, measurement of the magnitudes of impedance in response to a low frequency injection current and to a high frequency injection current, and calculating the difference between the impedance magnitudes, can produce an indicator of disease such as heart failure, pulmonary edema, or others.

Figure 4:
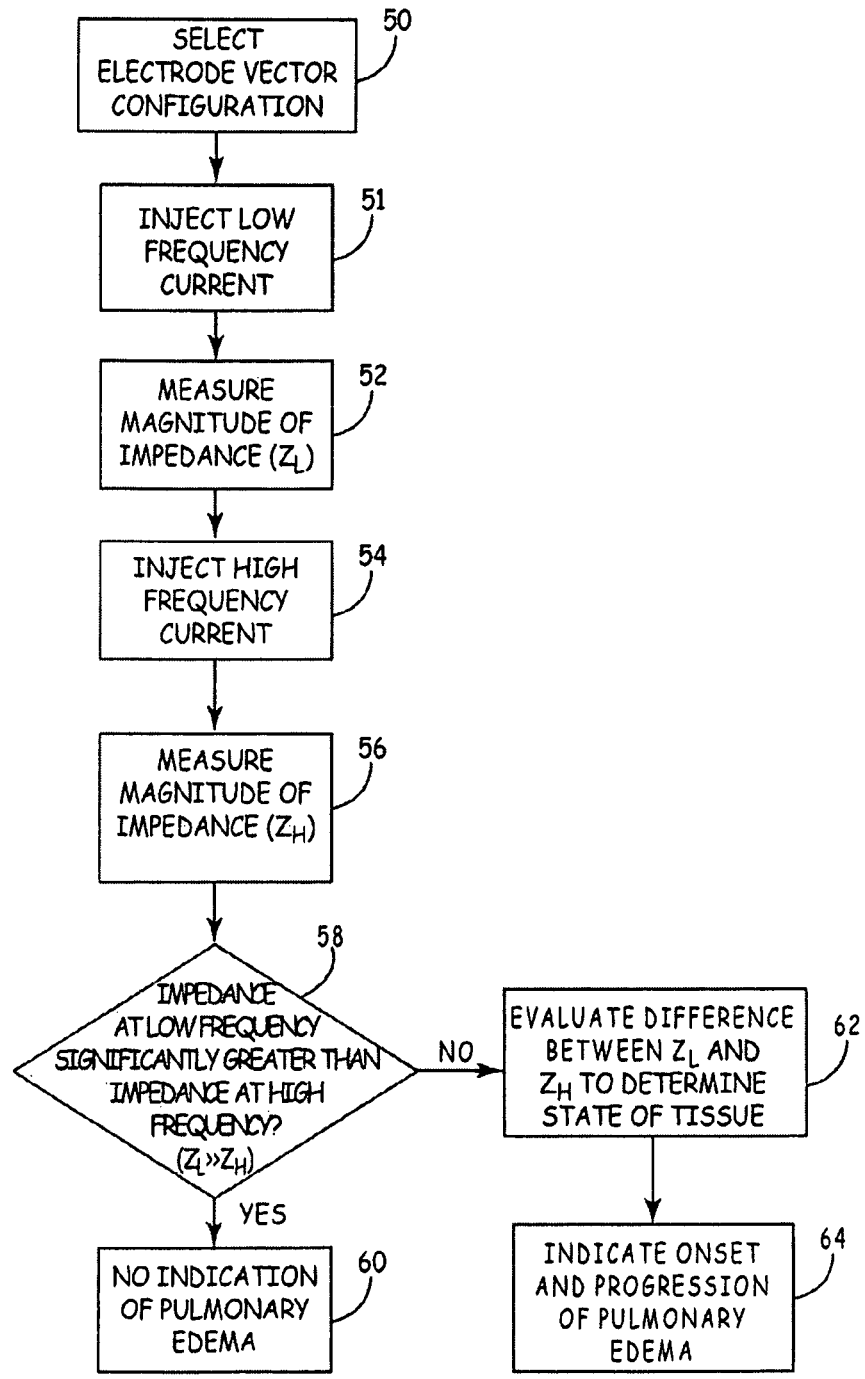
FIG. 4 is a flow diagram illustrating an example of a method of monitoring the difference between impedance magnitudes at low and high injection current frequencies.

FIG. 4 is a flow diagram illustrating an example of a method of monitoring the difference between impedance magnitudes at low and high injection current frequencies. After an electrode vector configuration is selected (step 50), a low frequency current is injected into ah electrode pair (step 51), and the magnitude of the impedance ($Z_L$) at low frequency is measured (step 52). Then, a high frequency current is injected into the electrode pair (step 54), and the magnitude of the impedance ($Z_H$) at high frequency is measured (step 56). The low frequency impedance ($Z_L$) is then compared to the high frequency impedance ($Z_H$) (step 58). If the low frequency impedance. ($Z_L$) is significantly greater than the high frequency impedance ($Z_H$), then conditions are normal and there is no indication of heart failure or pulmonary edema (step 60). However, if the low frequency impedance ($Z_L$) is not significantly greater than the high frequency impedance ($Z_H$), then the difference between the low frequency impedance ($Z_L$) and the high frequency impedance ($Z_H$) is evaluated to determine the state of the tissue (step 62). From this evaluation, the onset and progression of disease such as heart failure or pulmonary edema is indicated (step 64). For example, a smaller difference between the low frequency impedance ($Z_L$) and the high frequency impedance ($Z_H$) may indicate a more advanced progression of heart failure or, more specifically, pulmonary edema.

In an exemplary embodiment, with respect to the injection currents described above, the low frequency is no greater than about 10 kiloHertz, and the high frequency is about ten times greater than the low frequency, such as between about 50 kiloHertz and 100 kiloHertz.

Measurement of Real and Reactive Components of Impedance at Low Frequency

Figure 5:
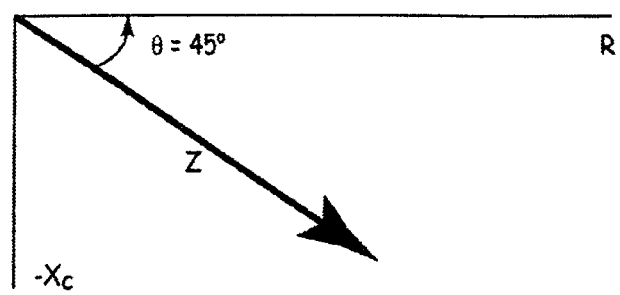
FIG. 5 is a phasor diagram illustrating the real component and the reactive component of impedance measured in response to a low frequency injection current in healthy tissue.
Figure 6:
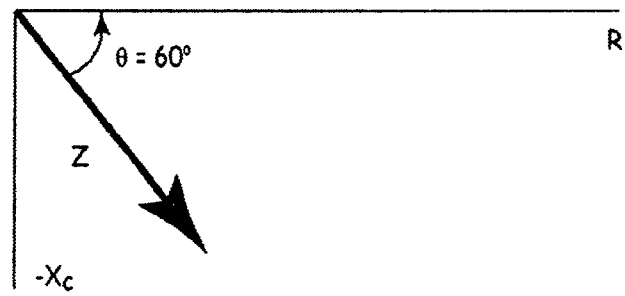
FIG. 6 is a phasor diagram illustrating the real component and the reactive component of impedance measured in response to a low frequency injection current in diseased tissue such as in pulmonary fluid congestion.

FIGS. 5 and 6 are exemplary phasor diagrams illustrating the real component (R) and the reactive component ($X_C$) of impedance (Z), measured in response to a low frequency injection current in healthy tissue (FIG. 5) and in diseased tissue having fluid accumulated in extracellular spaces (FIG. 6). The impedance (Z) is calculated according to the following formula:

$$Z = \sqrt{(R^2 + X_C^2)} \quad \text{(Eq. 1).}$$

The corresponding phase angle (θ) of the impedance phasor is calculated according to the following formula:

$$\theta = \tan^{-1}(X_C/R)$$

As can be seen from the examples in FIGS. 5 and 6, the accumulation of fluid in extracellular spaces results in an increase in the phase angle (θ) of the impedance phasor (such as from 45° for healthy tissue in FIG. 5 to 60° for diseased tissue in the example of FIG. 6), and also in a decrease in the total magnitude of impedance (Z), due to a decrease in the real component (R) of impedance caused by a decrease in the extracellular volumes of the cells, which causes the cells' extracellular resistance to decrease. The increase in phase angle or the decrease in impedance magnitude (or both) is detectable as an indication of the onset or progression of a cardiopulmonary disease such as pulmonary edema secondary to heart failure.

Figure 7:
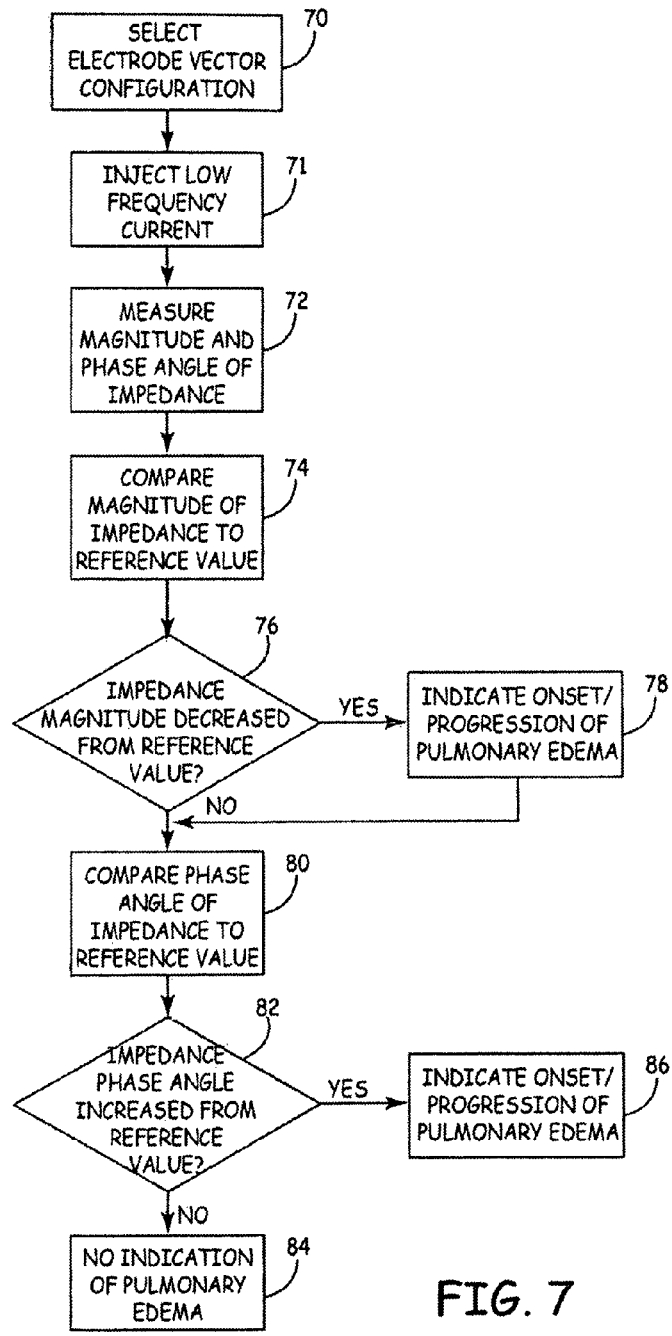
FIG. 7 is a flow diagram illustrating an example of a method of monitoring changes in phase angle and/or impedance magnitude in response to low frequency injection current in order to detect pulmonary edema.

FIG. 7 is a flow diagram illustrating an example of a method of monitoring changes in phase angle and/or impedance magnitude in response to low frequency injection current in order to detect pulmonary edema. After an electrode vector configuration is selected (step 70), a low frequency current is injected into an electrode pair (step 71), and the magnitude and phase angle of the impedance is measured (step 72). The magnitude of the impedance is then compared to a reference value (step 74), and it is determined whether the magnitude of the impedance has decreased from the reference value (step 76). If the impedance has decreased from the reference value, the onset/progression of pulmonary edema and the like is indicated (step 78).

The next step is to compare the phase angle of the impedance to a reference value (step 80), and to determine whether the phase angle has increased from the reference value (step 82), which would indicate that the real component of the impedance has decreased in comparison to the reactive component of the impedance (see FIGS. 5 and 6). If the phase angle of the impedance has not increased from the reference value, there is no indication of pulmonary edema (step 84). If the phase angle of the impedance has increased from the reference value, the onset/progression of pulmonary edema is indicated (step 86).

A method according to FIG. 7 shows separate determinations of the onset/progression of pulmonary edema based on the magnitude and the phase angle of impedance. In some embodiments, a determination of either a decreased magnitude of impedance or an increased phase angle of impedance will result in an indication of the onset/progression of pulmonary edema. In other embodiments, both a decrease in the magnitude of impedance and an increase in the phase angle of impedance are required to indicate the onset/progression of pulmonary edema. In still further embodiments, separate indications of the onset/progression of pulmonary edema based on a relative change in the magnitude of impedance and the phase angle of impedance are provided.

Measurement of Real and Reactive Components of Impedance at High Frequency

Figure 8:
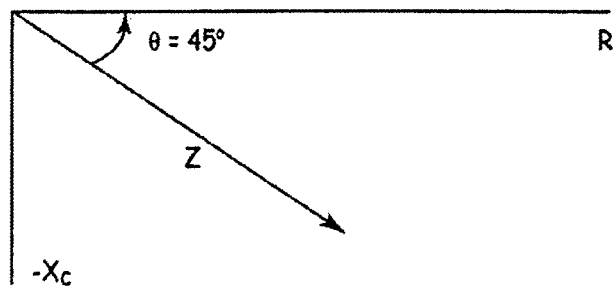
FIG. 8 is a phasor diagram illustrating the real component and the reactive component of impedance measured in response to a high frequency injection current in healthy tissue.
Figure 9:
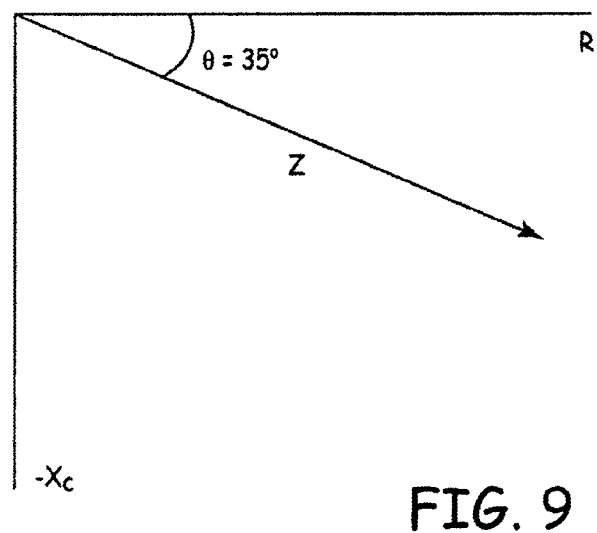
FIG. 9 is a phasor diagram illustrating, the real component and the reactive component of impedance measured in response to a high frequency injection current in diseased tissue such as myocardial ishemia.

FIGS. 8 and 9 are phasor diagrams illustrating the real component (R) and the reactive component ($X_C$) of impedance (Z), measured in response to a high frequency injection current in healthy tissue (FIG. 8) and in diseased tissue such as in myocardial ischemia (FIG. 9). The impedance (Z) and phase angle (θ) are calculated according to Eq. 1 and Eq. 2 above, respectively. As can be seen from the examples shown in FIGS. 8 and 9, ischemia in the tissue results in a decrease in the phase angle (θ) of the impedance phasor (such as from 45° for healthy tissue in FIG. 8 to 35° for ischemic tissue in FIG. 9), and also in an increase in the total magnitude of impedance (Z), due to an increase in the resistive component (R) of impedance caused by decreased extracellular volume. The decrease in phase angle or the increase in impedance magnitude (or both) is detectable as a potential indicator of myocardial ischemia.

Over time, the cells in ischemic tissue will rupture, so that intracellular and extracellular fluid drains out the lymphatic system. This causes the real component (R) of impedance to increase due to the decreased volume of the cell, and also causes the reactive component ($X_C$) of impedance to increase due to the decreased surface area of the cell. As a result, the total magnitude of impedance increases significantly, which is detectable as a potential indicator of myocardial necrosis or myocardial infarct.

Figure 10:
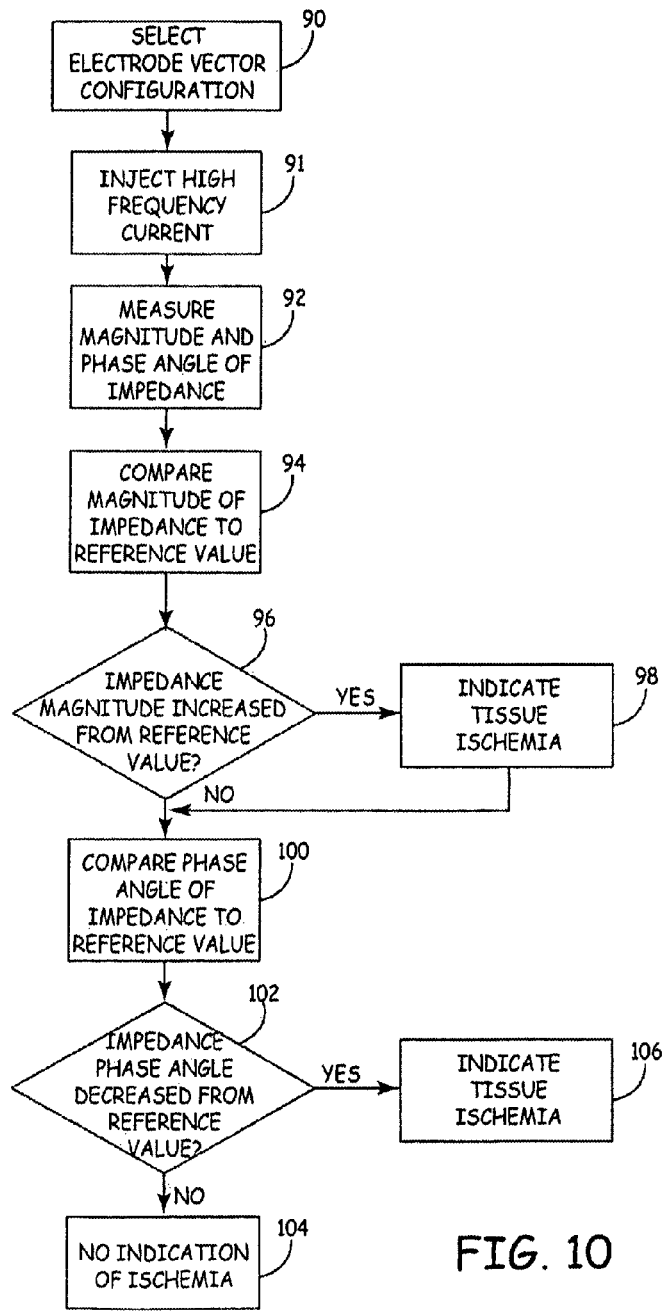
FIG. 10 is a flow diagram illustrating an example of a method of monitoring changes in phase angle and/or impedance magnitude in response to high frequency injection current in order to detect myocardial ischemia.

FIG. 10 is a flow diagram illustrating an example of a method of monitoring changes in phase angle and/or impedance magnitude in response to high frequency injection current in order to detect disease such as myocardial ischemia. After an electrode vector configuration is selected (step 90), a high frequency current is injected into an electrode pair (step 91), and the magnitude and phase angle of the impedance is measured (step 92). The magnitude of the impedance is then compared to a reference value (step 94), and it is determined whether the magnitude of the impedance has increased from the reference value (step 96). If the impedance has increased from the reference value, an indication of tissue ischemia is made (step 98).

The next step is to compare the phase angle of the impedance to a reference value (step 100), and to determine whether the phase angle has decreased from the reference value (step 102), which would indicate that the resistive component of the impedance has increased in comparison to the reactive component of the impedance (see FIGS. 8 and 9). If the phase angle of the impedance has not decreased from the reference value, there is no indication of tissue ischemia (step 104). If the phase angle of the impedance has decreased from the reference value, an indication of tissue ischemia is made (step 106).

A method according to FIG. 10 shows separate determinations of tissue ischemia based on the magnitude and the phase angle of impedance. In some embodiments, a determination of either an increased magnitude of impedance or a decreased phase angle of impedance will result in an indication of tissue ischemia. In other embodiments, both an increase in the magnitude of impedance and a decrease in the phase angle of impedance are required to indicate tissue ischemia. In still further embodiments, separate indications of tissue ischemia based on a relative change in the magnitude of impedance and the phase angle of impedance are provided.

Electrode Placement and Vector Selection

Figure 11A:
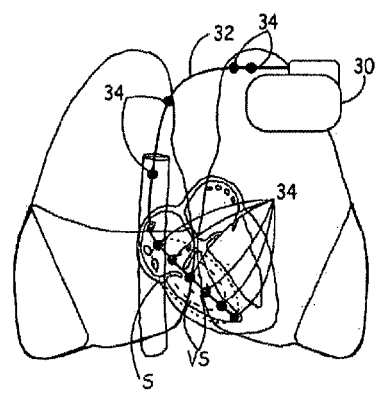
FIGS. 11A-11D are diagrams showing examples of uses of electrodes configured as shown in FIG. 2 with a lead extending into the right ventricle (RV) and electrodes carried by the lead positioned in the RV, the right atrium, the superior vena cava and the subclavian vein.
Figure 11B:
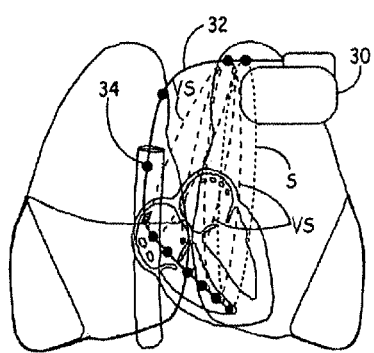
Figure 11C:
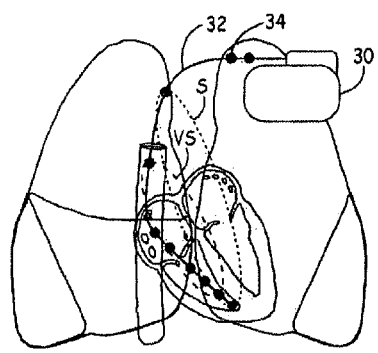
Figure 11D:
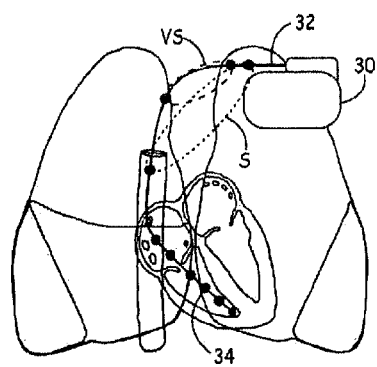

As discussed above, FIG. 2 illustrates an example of the relative placement of IMD 30 and lead 32 carrying electrodes 34 for performing an intrathoracic impedance measurement, with lead 32 extending into the right ventricle (RV), and electrodes 34 positioned in the RV, the right atrium; the superior vena cava and the subclavian vein. FIGS. 11A-11D show examples of how electrodes 34 may be used in this configuration. FIG. 11A illustrates a scenario in which a stimulation vector (S) is established between an electrode in the right atrium (RA) and an electrode in the RV, so that transvalvular impedance can be measured by voltage sense vectors (VS). FIG. 11B illustrates a scenario in which a stimulation vector (S) is established between an electrode adjacent to IMD 30 and an electrode in the RV, so that left heart impedance can be measured by voltage sense vectors (VS). FIG. 11C illustrates a scenario in which a stimulation vector (S) is established between an electrode in the superior vena cava and an electrode in the RV, so that right heart impedance can be measured by a voltage sense vector (VS). FIG. 11D illustrates a scenario in which a stimulation vector (S) is established between an electrode adjacent to IMD 30 and an electrode in the superior vena cava, so that superior lung impedance can be measured by a voltage sense vector (VS).

Figure 12:
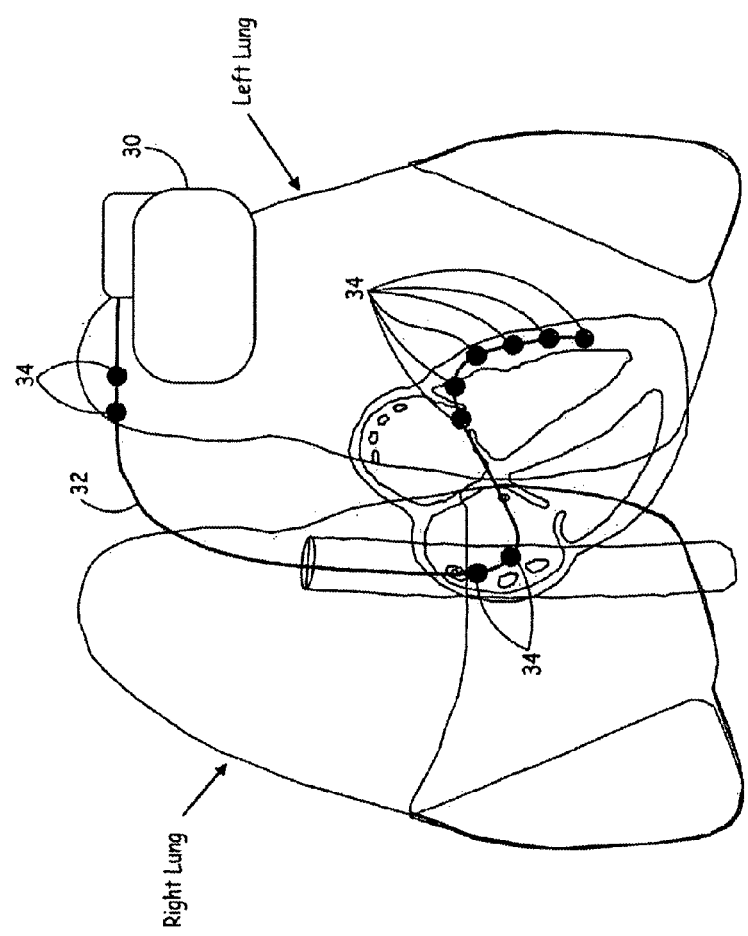
FIG. 12 is a diagram illustrating another example of the relative placement of an IMD and a lead carrying electrodes for performing an intrathoracic impedance measurement.
Figure 13A:
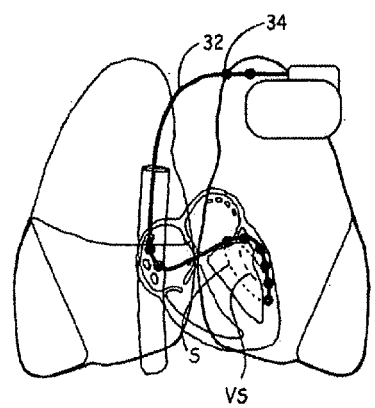
FIGS. 13A-13D are diagrams showing examples of uses of electrodes configured as shown in FIG. 12 with a distal end of a lead placed over the left ventricle (LV) via the cardiac vein, and electrodes carried by the lead positioned over the LV, in the right atrium, in the subclavian vein, and adjacent to an IMD.
Figure 13B:
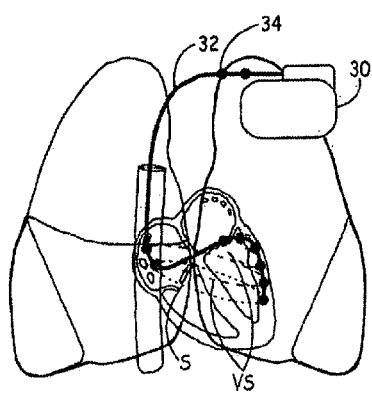
Figure 13C:
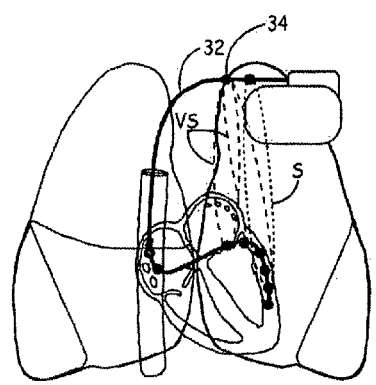
Figure 13D:
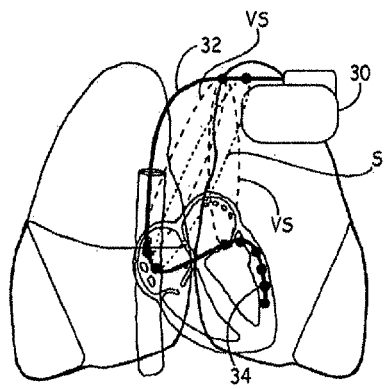

FIG. 12 illustrates another example of the relative placement of IMD 30 and lead 32 carrying electrodes 34 for performing an intrathoracic impedance measurement, with the distal end of lead 32 placed over the left ventricle (LV) via the cardiac vein, and electrodes 34 positioned over the LV, in the right atrium, and in the subclavian vein. FIGS. 13A-13D show examples of how electrodes 34 may be used in this configuration. FIG. 13A illustrates a scenario in which a stimulation vector (S) is established between two electrodes spanning the LV, so that LV impedance can be measured by voltage sense vectors (VS). FIG. 13B illustrates a scenario in which a stimulation vector (S) is established between a distal electrode adjacent the LV and an electrode in the right atrium (RA), so that right atrial impedance can be measured by voltage sense vectors (VS). FIG. 13C illustrates a scenario in which a stimulation vector (S) is established between a distal electrode adjacent the LV and an electrode adjacent IMD 30, so that left lung impedance can be measured by voltage sense vectors (VS). FIG. 13D illustrates a scenario in which a stimulation vector (S) is established between an electrode in the RA and an electrode adjacent IMD 30, so that superior left lung impedance can be measured by voltage sense vectors (VS). Lead 32 may alternatively be positioned to provide electrodes 34 epicardially over the LV to allow similar measurements.

Figure 14:
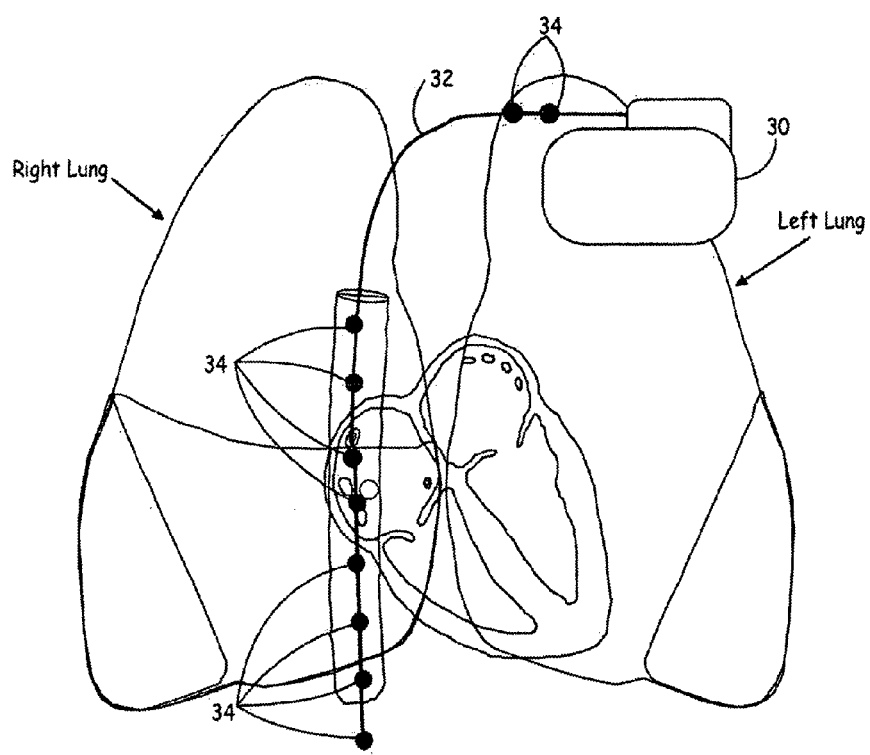
FIG. 14 is a diagram illustrating another example of the relative placement of an IMD and a lead carrying electrodes for performing an intrathoracic impedance measurement.
Figures 15A, 15B:
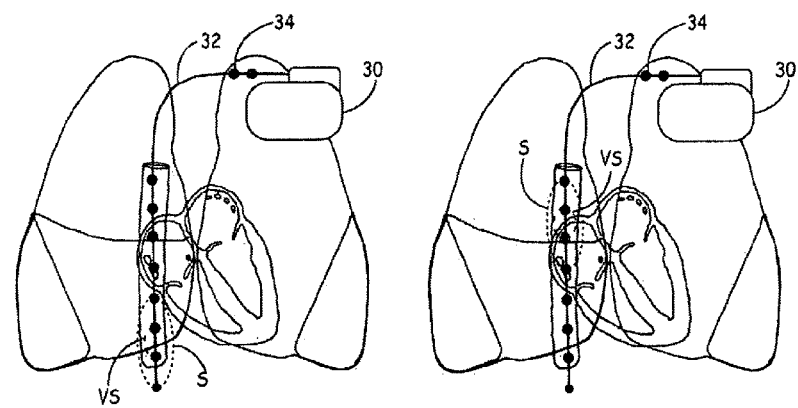
FIGS. 15A-15D are diagrams showing examples of uses of electrodes configured as shown in FIG. 14 with a distal end of a lead placed in the inferior vena cava (IFC) and electrodes carried by the lead positioned in the IVC, the right atrium, the superior vena cava and the subclavian vein.
Figures 15C, 15D:
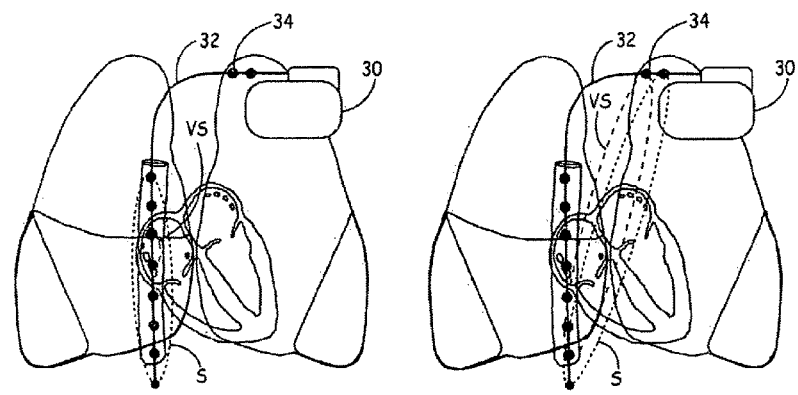

FIG. 14 illustrates another example of the relative placement of IMD 30 and lead 32 carrying electrodes 34 for performing an intrathoracic impedance measurement, with the distal end of lead 32 placed in the inferior vena cava (IVC), and electrodes 34 positioned in the IVC, right atrium, superior vena cava and subclavian vein. FIGS. 15A-15D show examples of how electrodes 34 may be used in this configuration, FIG. 15A illustrates a scenario in which a stimulation vector (S) is established between two electrodes spanning the IVC, so that IVC impedance can be measured by a voltage sense vector (VS). FIG. 15B illustrates a scenario in which a stimulation vector (S) is established between an electrode in the RA and an electrode in the superior vena cava, so that superior vena cava impedance can be measured by a voltage sense vector (VS). FIG. 15C illustrates a scenario in which a stimulation vector (S) is established between an electrode in the IVC and an electrode in the superior vena cava, so that central venous impedance can be measured by a voltage sense vector (VS). FIG. 15D illustrates a scenario in which a stimulation vector (S) is established between an electrode in the IVC and an electrode in adjacent to IMD 30, so that atrial impedance can be measured by a voltage sensor vector (VS).

Figure 16:
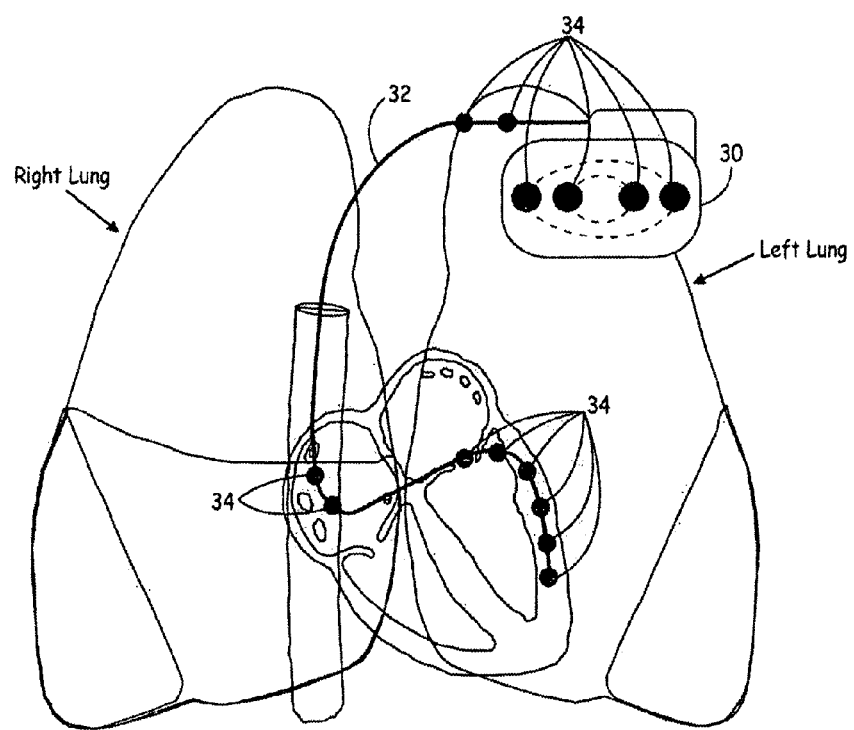
FIG. 16 is a diagram illustrating another example of the relative placement of an IMD and a lead carrying electrodes for performing an intrathoracic impedance measurement.
Figures 17A, 17B:
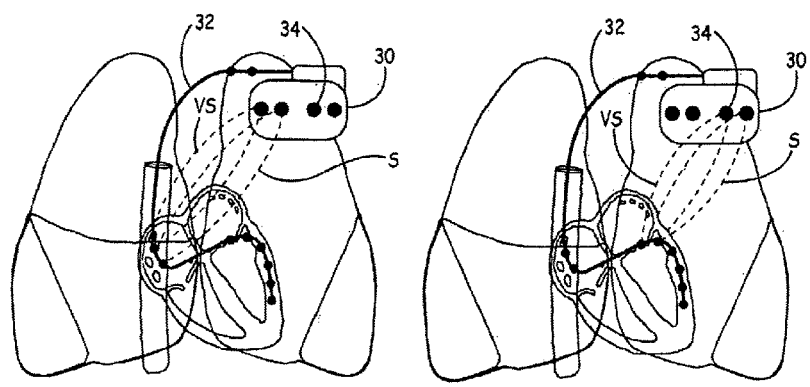
FIGS. 17A, 17B and 17C are diagrams showing examples of uses of electrodes configured as shown in FIG. 16 with electrodes carried on the IMD housing implanted subcutaneously in the left lateral superior thorax, with a distal end of the lead placed over the left ventricle (LV) via the cardiac vein, and with electrodes carried by the lead positioned over the LV, in the right atrium, and in the subclavian vein.
Figure 17C:
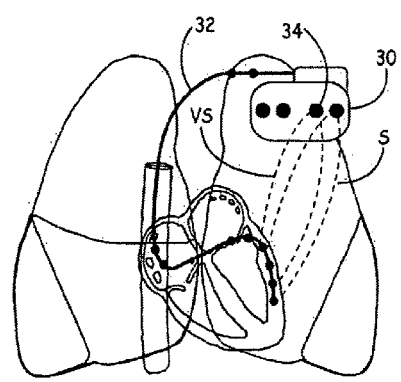

FIG. 16 illustrates another example of the relative placement of IMD 30 carrying electrodes 34 and lead 32 carrying electrodes 34 for performing an intrathoracic impedance measurement, with electrodes 34 carried by the housing (or "can") of IMD 30 implanted subcutaneously in the left lateral superior thorax, with a distal end of lead 32 placed over the left ventricle (LV) via the cardiac vein, and with electrodes 34 carried by lead 32 positioned over the LV, in the right atrium (RA), and in the subclavian vein. FIGS. 17A-17C show examples of how electrodes 34 maybe used in this configuration. FIG. 17A illustrates a scenario in which a stimulation vector (S) is established between an electrode in the RA and an electrode carried by the housing of IMD 30, so that upper lung impedance or RA function can be measured by voltage sense vectors (VS). FIG. 17B illustrates a scenario in which a stimulation vector (S) is established between an electrode in the posterior coronary sinus or applicable cardiac vein and an electrode carried by the housing of IMD 30, so that middle lung impedance can be measured by voltage sense vectors (VS). FIG. 17C illustrates a scenario in which a stimulation vector (S) is established between a distal electrode in the subclavian vein adjacent the LV and an electrode carried by the housing of IMD 30, so that lower lung impedance can be measured by voltage sense vectors (VS).

Figure 18:
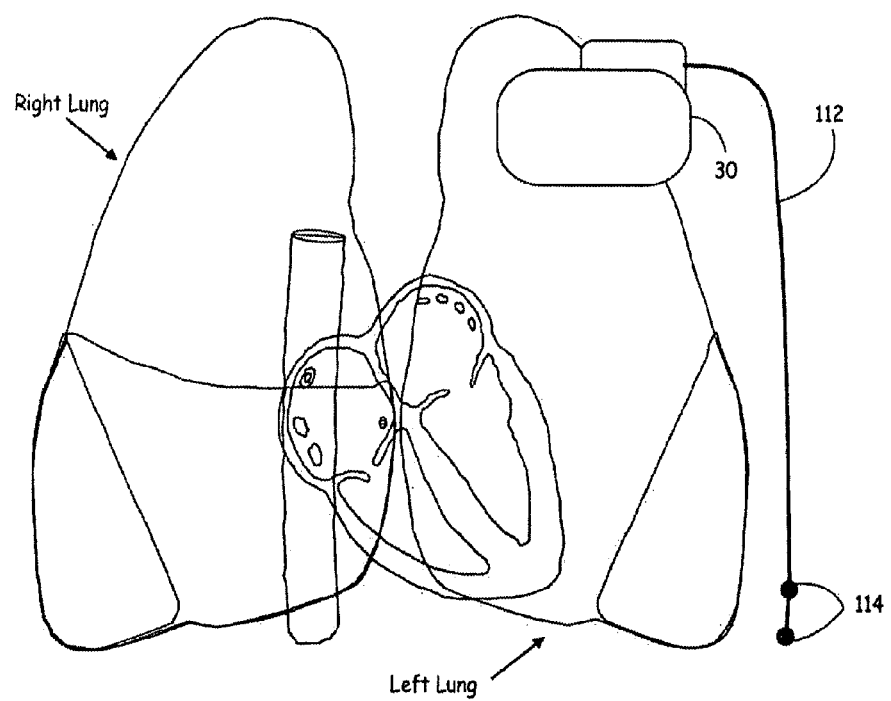
FIG. 18 is a diagram illustrating an example of a subcutaneous lead configured with its distal end placed in the left lateral thorax.
Figures 19A, 19B:
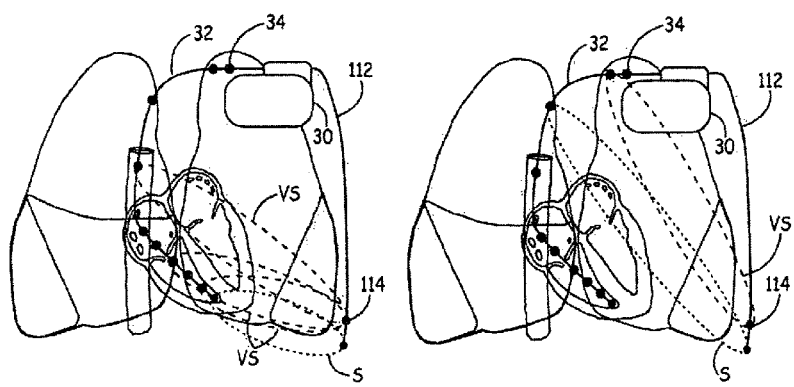
FIGS. 19A and 19B are diagrams showing examples of uses of electrodes configured as shown in FIG. 2 in conjunction with the subcutaneous lead configuration shown in FIG. 18.
Figures 19C, 19D:
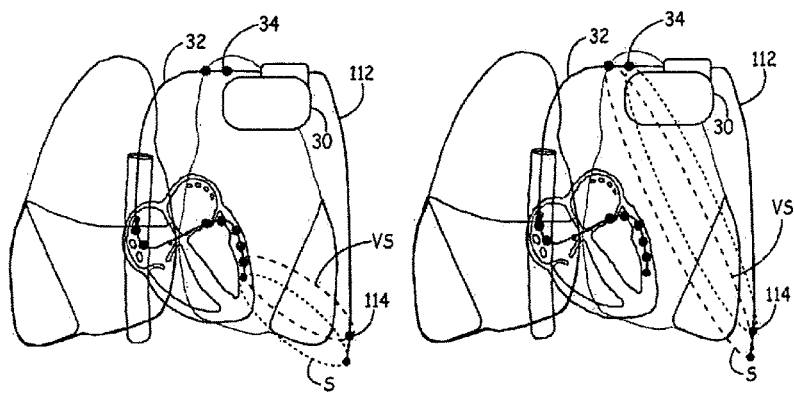
FIGS. 19C and 19D are diagrams showing examples of uses of electrodes configured as shown in FIG. 12 in conjunction with the subcutaneous lead configuration shown in FIG. 18.

FIG. 18 illustrates an example of subcutaneous lead 112 configured with its distal end (carrying electrodes 114) placed in the left lateral thorax. When lead 112 is used in conjunction with intrathoracic lead 32 and electrodes 34, left heart and left lung zones can be isolated for impedance measurements. FIGS. 19A and 19B show examples of how electrodes 34 and 114 may be used in this configuration, where lead 32 and electrodes 34 are arranged as shown in FIG. 2. FIG. 19A illustrates a scenario in which a stimulation vector (S) is established between an electrode in the RV and the distal electrode in the left lateral thorax, so that left heart and inferior left lung impedance can be measured by voltage sense vectors (VS). FIG. 19B illustrates a scenario in which a stimulation vector (S) is established between an electrode in the superior vena cava and the distal electrode in the left lateral thorax, so that left lung impedance can be measured by voltage sense vectors (VS). FIGS. 19C and 19D show examples of how electrodes 34 and 114 may be used where lead 32 and electrodes 34 are arranged as shown in FIG. 12. FIG. 19C illustrates a scenario in which a stimulation vector (S) is established between an electrode adjacent the LV and the distal electrode in the left lateral thorax, so that lower left lung impedance can be measured by a voltage sense vector (VS). FIG. 19D illustrates a scenario in which a stimulation vector (S) is established between an electrode in the upper left lung and the distal electrode in the left lateral thorax, so that upper left lung impedance can be measured by a voltage sense vector (VS). With this arrangement and the scenarios shown in FIGS. 19C and 19D, the vector configuration shown in FIG. 19D (measuring upper left lung impedance) can be used as a reference vector for comparison with the vector configuration shown in FIG. 19C (measuring lower left lung impedance), and the ratio of the two impedance vectors can be used as an index of the progression of fluid accumulation in zones of the left lung.

Vector Selection Based on Cardiac and Respiratory Components of Waveform

Figure 20:
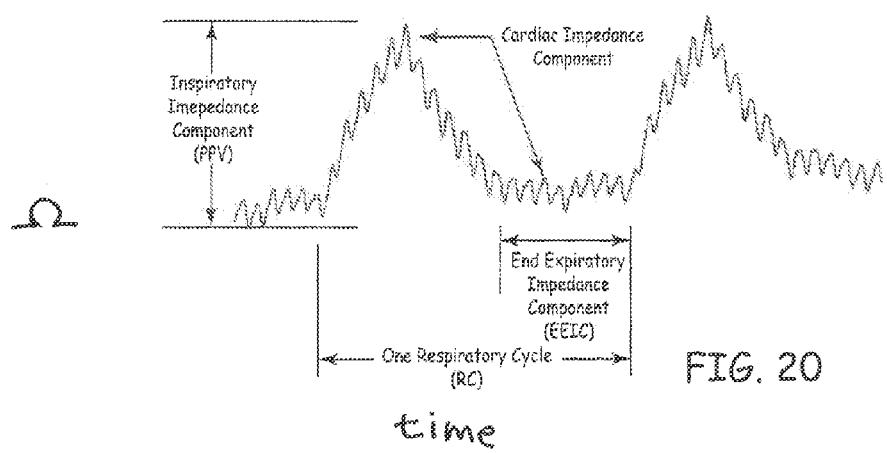
FIG. 20 is a diagram illustrating an example of an impedance waveform containing a high frequency cardiac component superimposed on a low frequency respiratory component and a DC or mean component.

The impedance waveforms measured via the electrode configurations discussed above contain a high frequency cardiac component superimposed on a low frequency respiratory component and a calculated DC or mean component. FIG. 20 is a diagram illustrating an example of such ah impedance waveform. Each of the components of the impedance waveform has potential clinical diagnostic utility (for example, diagnostics for detecting various conditions are discussed above). The relative magnitude of each component of the impedance waveform depends on the geometric electrode configuration. In order to select a particularly useful electrode vector from a group of vectors, the ratio of the magnitude of the cardiac impedance component to the magnitude of the respiratory impedance component (CC/RC) is analyzed for each vector, and the vector having the highest CC/RC ratio is selected as the most useful for analysis of the impedance waveform for the selected tissue segment.

Geometric vector configurations may be selected to identify the most useful electrode vector for diagnostic monitoring of the lung for fluid accumulation and respiration, the myocardium for ischemia, or the cardiac chambers for contractility, stroke volume, dilation, or arrhythmia identification. The measurement of impedances in these regions is useful to measure fluid compartmentalization shifts in patients with congestive heart failure or pulmonary edema, or to isolate a specific section of the myocardium to detect ischemia, for example. A detailed discussion of analyzing the morphology of various components of complex impedance waveforms to determine changes in physiologic parameters that may indicate the onset or progression of various clinical conditions may be found in U.S. application Ser. No. 12/112, 655 filed on even date herewith, for "System And Method Of Detecting Physiologic Parameters Based On Complex Impedance Waveform Morphology" by T. Zielinski, D. Hettrick and E. Warman.

The impedance waveform shown in FIG. 20 may be obtained from a subcutaneous, intracardiac, or combination thereof electrode vector configuration. Two positive pressure ventilation (PPV) respiratory cycles are shown. Parameters illustrated in FIG. 20 include a respiratory cycle (RC) time, an end expiratory impedance component (EEIC) time, and an inspiratory impedance component (labeled as PPV). Cardiac impedance components appear as high frequency components of the waveform.

Figure 21:
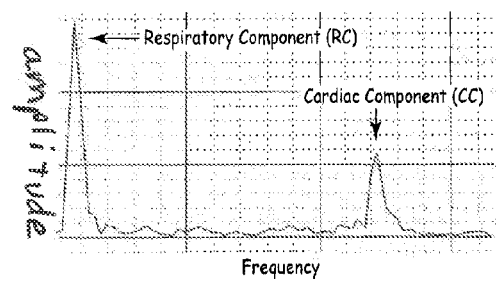
FIG. 21 is a diagram illustrating a Fast Fourier Transform (FFT) analysis of the impedance waveform shown in FIG. 20.

FIG. 21 is a diagram illustrating a Fast Fourier Transform (FFT) analysis of the impedance waveform shown in FIG. 20. As shown in the diagram, the high frequency cardiac component (CC) of the impedance waveform is easily visible and separated from the low frequency respiratory component (RC) of the impedance waveform. A FFT analysis is one example of a method that can be used to calculate the ratio of the magnitude of the high frequency CC of impedance to the low frequency RC of impedance, to identify an electrode vector having the highest CC/RC ratio for selection to analyze and identify certain physiological conditions and disease states.

Figure 22:
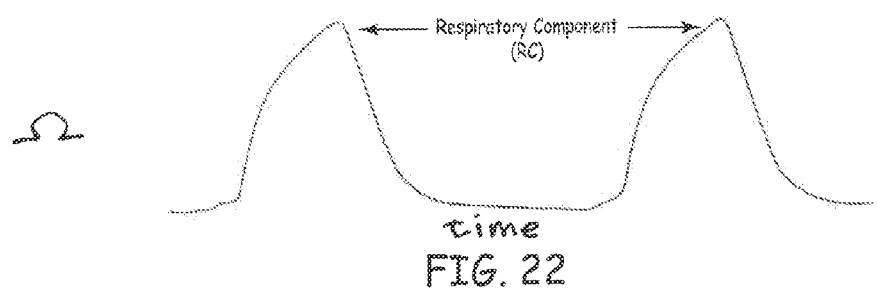
FIG. 22 is a diagram illustrating an example of an impedance waveform obtained from a transthoracic subcutaneous electrode vector configuration utilizing electrodes positioned substernal and bilateral on the left and right thorax.
Figure 23:
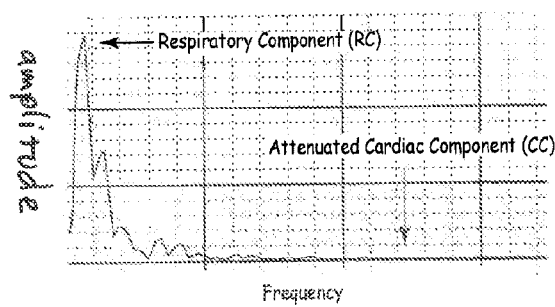
FIG. 23 is a diagram illustrating a FFT analysis of the impedance waveform shown in FIG. 22 where the high frequency cardiac component is attenuated.

FIG. 22 is a diagram illustrating an example of an impedance waveform obtained from a transthoracic subcutaneous electrode vector configuration utilizing electrodes positioned substernal and bilateral on the left and right thorax. As can be seen in FIG. 22, the impedance waveform has a highly attenuated high frequency cardiac component (CC), such that only the low frequency respiratory component (RC) of the impedance waveform is even observable. FIG. 23 is a diagram illustrating a Fast Fourier Transform (FFT) analysis of the impedance waveform shown in FIG. 22. As shown in the diagram, the high frequency CC of the impedance waveform is attenuated and not observable, while the low frequency RC of the impedance waveform is easily observable. Thus, the CC/RC ratio in this scenario is low, and this electrode vector would typically not be selected for analysis in order to determine physiological conditions and disease states.

Figure 24:
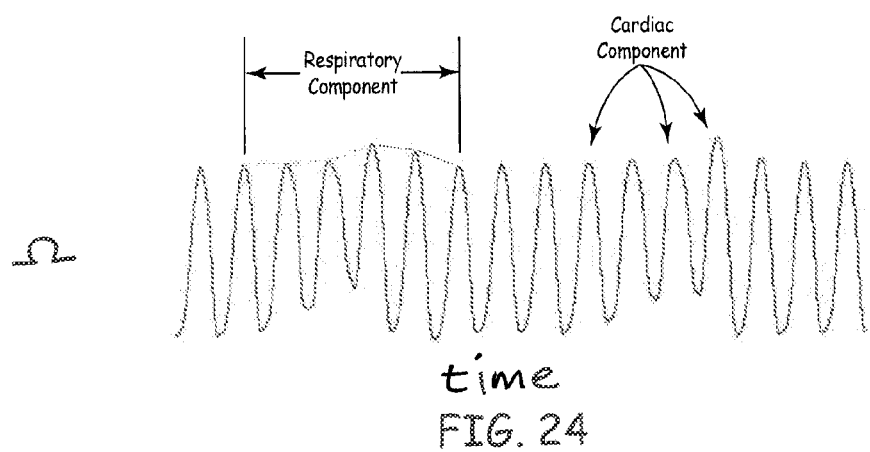
FIG. 24 is a diagram illustrating an example of an impedance waveform obtained from a combination subcutaneous and intracardiac electrode vector configuration utilizing electrodes positioned in the right ventricle, the left ventricle, and the device housing.
Figure 25:
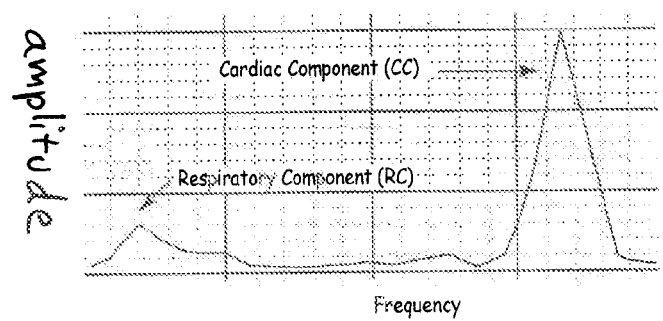
FIG. 25 is a diagram illustrating a FFT analysis of the impedance waveform shown in FIG. 24.

FIG. 24 is a diagram illustrating an example of an impedance waveform obtained from a combination subcutaneous and intracardiac electrode vector configuration utilizing electrodes positioned in the right ventricle, the left ventricle, and the device housing. As can be seen in FIG. 24, the impedance Waveform has a significant, observable high frequency cardiac component (CC), and a relatively small low frequency respiratory component (RC) of the impedance waveform is observable. FIG. 25 is a diagram illustrating a Fast Fourier Transform (FFT) analysis of the impedance waveform shown in FIG. 24. As shown in the diagram, the high frequency CC of the impedance waveform is significant and easily observable, separated from the relatively small low frequency RC of the impedance waveform. Thus, the CC/RC ratio in this scenario is high, and this electrode vector would highly likely to be selected for analysis in order to determine physiological conditions and disease states.

Figure 26:
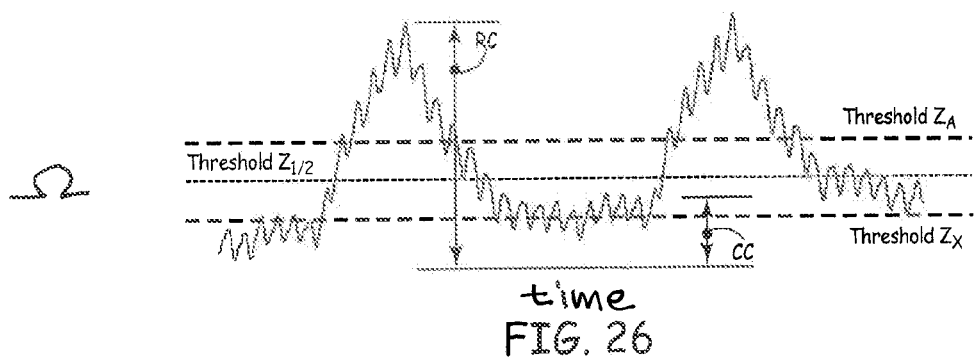
FIG. 26 is a diagram illustrating a method of calculating a ratio between the cardiac component and the respiratory component of an impedance waveform utilizing a threshold adjustment technique.
Figure 27:
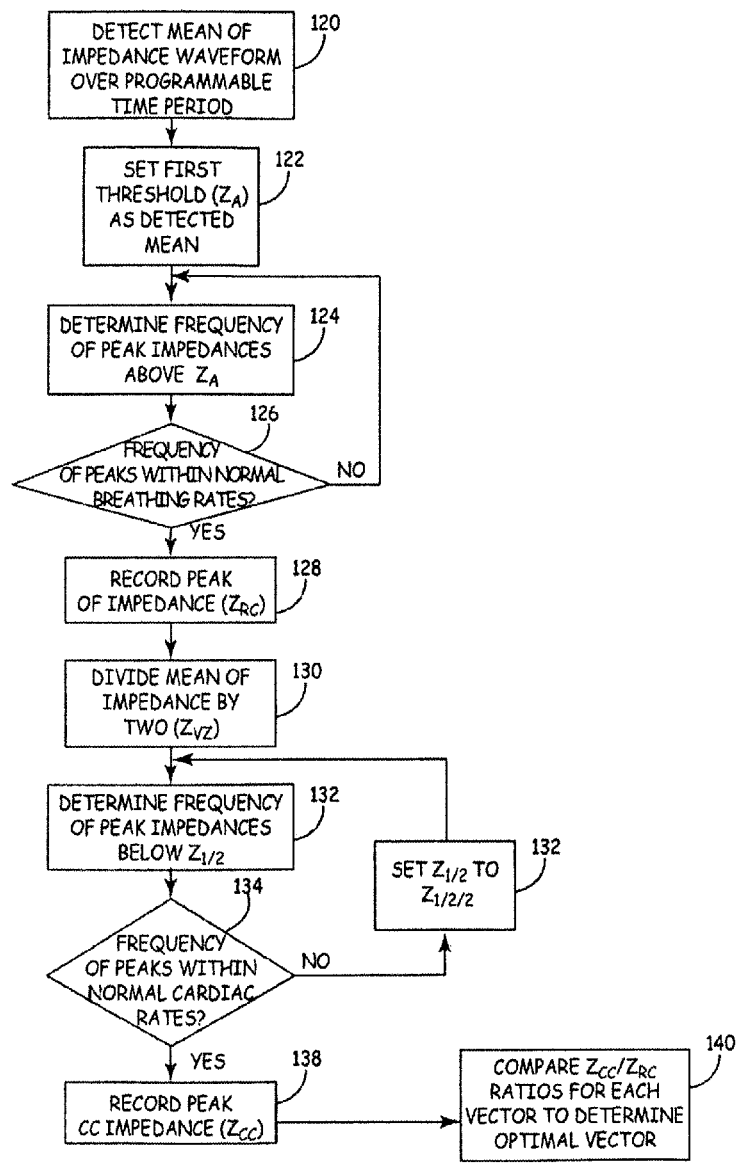
FIG. 27 is a flow diagram illustrating a method of detecting the peak of the respiratory component of the impedance waveform during end inspiration and of detecting the peak impedance of the cardiac component of the impedance waveform during end expiration.

FIG. 26 is a diagram illustrating a method of calculating a CC/RC ratio of an impedance waveform utilizing a threshold adjustment technique. The peak impedance of the RC of the impedance waveform is detected and measured during end inspiration, and the peak impedance of the CC of the impedance waveform is detected and measured during, end expiration. This method is performed as shown in the flowchart of FIG. 27. First, the mean of the impedance waveform is detected over a programmable time period, such as fifteen seconds in one embodiment (step 120). The detected mean is then set as a first threshold ($Z_A$, see FIG. 26; step 122). A peak detection algorithm, as is generally known in the art, then determines the frequency of the peak impedances (step 124) and identifies whether the determined frequency is within the limits of normal breathing rates (such as below 40 breaths per minute in one example; step 126). The peak impedance of the RC is then recorded ($Z_{RC}$, see FIG. 26; step 128). Once this peak is determined, the mean impedance is divided by two ($Z_{1/2}$, see FIG. 26; step 130). Then the peak detection algorithm is again performed to determine the frequency of the peak impedances below $Z_{1/2}$ (step 132). The algorithm identifies whether the determined frequency is within the limits of normal cardiac rates (such as above 50 beats per minute in one example; step 134), and if it is not, the threshold is again divided by two (step 136) and the process is repeated. Once a valid frequency is determined, the peak impedance of the CC ($Z_{CC}$) is recorded (step 138). These impedance magnitudes for each vector are then used to determine the optimal electrode vector configuration based on the $Z_{CC}/Z_{RC}$ ratio of each vector (step 140).

The system(s) and method(s) described above provide an improved ability to measure complex intrathoracic impedance and to identify and predict disease conditions based on the impedance measurements. Multiple impedance vectors may be taken into account, and an optimal vector may be selected to provide the most useful impedance measurement for the identification and prediction of disease conditions.

Although the present invention has been described with reference to preferred embodiments, workers skilled in the art will recognize that changes may be made in form and detail without departing from the spirit and scope of the invention.

The invention claimed is:

1. A method of determining and indicating a disease condition, the method comprising:
   injecting a first current having a first frequency between a pair of electrodes having a tissue segment therebetween wherein the pair of electrodes is positioned for intrathoracic impedance measurement;
   measuring a magnitude and a phase angle of impedance in the tissue segment at the first frequency;
   comparing at least one of the measured magnitude of impedance and the measured phase angle of impedance at the first frequency to a reference value of impedance magnitude and a reference value of impedance phase angle, respectively, established at the first frequency;
   evaluating at least one of a difference between the measured magnitude of impedance and the reference value of impedance magnitude, and a difference between the measured phase angle of impedance and the reference value of impedance phase angle, to determine whether the tissue segment is in a diseased condition;
   providing an indicator of disease based on the determination of whether the tissue is in a diseased condition; and
   wherein the first frequency is a low frequency no greater than about 10 kiloHertz, and an indicator of pulmonary edema is provided based on an increase in the measured phase angle of impedance from the reference value of impedance phase angle.

2. A method of determining and indicating a disease condition, the method comprising:
   injecting a first current having a first frequency between a pair of electrodes having a tissue segment therebetween wherein the pair of electrodes is positioned for intrathoracic impedance measurement;

measuring a magnitude and a phase angle of impedance in the tissue segment at the first frequency;

comparing at least one of the measured magnitude of impedance and the measured phase angle of impedance at the first frequency to a reference value of impedance magnitude and a reference value of impedance phase angle, respectively, established at the first frequency;

evaluating at least one of a difference between the measured magnitude of impedance and the reference value of impedance magnitude, and a difference between the measured phase angle of impedance and the reference value of impedance phase angle, to determine whether the tissue segment is in a diseased condition;

providing an indicator of disease based on the determination of whether the tissue is in a diseased condition; and wherein the first frequency is a low frequency no greater than about 10 kiloHertz, and an indicator of pulmonary edema is provided based on both a decrease in the measured magnitude of impedance from the reference value of impedance magnitude, and an increase in the measured phase angle of impedance from the reference value of impedance phase angle.

\* \* \* \* \*